(12) United States Patent
Akahori

(10) Patent No.: US 10,019,804 B2
(45) Date of Patent: Jul. 10, 2018

(54) MEDICAL IMAGE PROCESSING APPARATUS, METHOD, AND PROGRAM

(71) Applicant: FUJIFILM Corporation, Tokyo (JP)

(72) Inventor: Sadato Akahori, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 14/800,704

(22) Filed: Jul. 16, 2015

(65) Prior Publication Data

US 2015/0317799 A1 Nov. 5, 2015

Related U.S. Application Data

(63) Continuation of application No. PCT/JP2014/000076, filed on Jan. 10, 2014.

(30) Foreign Application Priority Data

Jan. 16, 2013 (JP) .................. 2013-005050

(51) Int. Cl.
*G06K 9/00* (2006.01)
*G06T 7/00* (2017.01)
(Continued)

(52) U.S. Cl.
CPC .......... *G06T 7/0081* (2013.01); *A61B 5/0035* (2013.01); *A61B 5/0044* (2013.01); *G06T 7/11* (2017.01); *G06T 7/149* (2017.01); *G06T 7/162* (2017.01); *G06T 7/174* (2017.01); *A61B 6/503* (2013.01); *G06T 2200/04* (2013.01);
(Continued)

(58) Field of Classification Search
None
See application file for complete search history.

(56) References Cited

U.S. PATENT DOCUMENTS

2003/0069494 A1* 4/2003 Jolly ................ A61B 5/055
600/410
2009/0161926 A1* 6/2009 Florin ................ A61B 8/00
382/128

(Continued)

FOREIGN PATENT DOCUMENTS

JP 2007-044346 2/2007
WO 2012/153539 11/2012

OTHER PUBLICATIONS

Karim, Rashed, et al. "Automatic segmentation of left atrial geometry from contrast-enhanced magnetic resonance images using a probabilistic atlas." International Workshop on Statistical Atlases and Computational Models of the Heart. Springer Berlin Heidelberg, 2010.*

(Continued)

*Primary Examiner* — Sean Conner
(74) *Attorney, Agent, or Firm* — JCIPRNET

(57) ABSTRACT

A medical image processing apparatus includes a medical image data obtaining unit for obtaining medical image data containing an image of a heart, and a region extraction processing unit for extracting a left ventricular region of the heart in the medical image data obtained by the medical image data obtaining unit, and, based on an extraction result of the left ventricular region, performing region extraction processing for extracting at least one of a right ventricular region, a left atrium region, and a right atrium region of the heart.

18 Claims, 5 Drawing Sheets

(51) Int. Cl.
  *A61B 5/00*  (2006.01)
  *G06T 7/11*  (2017.01)
  *G06T 7/149*  (2017.01)
  *G06T 7/162*  (2017.01)
  *G06T 7/174*  (2017.01)
  *A61B 6/00*  (2006.01)

(52) U.S. Cl.
  CPC ............ *G06T 2207/10004* (2013.01); *G06T 2207/10072* (2013.01); *G06T 2207/20072* (2013.01); *G06T 2207/20101* (2013.01); *G06T 2207/20128* (2013.01); *G06T 2207/30048* (2013.01)

(56) References Cited

U.S. PATENT DOCUMENTS

| | | | | |
|---|---|---|---|---|
| 2009/0290778 | A1* | 11/2009 | Sun | G06K 9/3233 |
| | | | | 382/131 |
| 2012/0281895 | A1* | 11/2012 | Chono | A61B 8/461 |
| | | | | 382/128 |
| 2013/0096414 | A1* | 4/2013 | Lu | A61B 5/0044 |
| | | | | 600/410 |
| 2014/0219524 | A1* | 8/2014 | Takeguchi | A61B 6/463 |
| | | | | 382/128 |

OTHER PUBLICATIONS

Mahapatra, Dwarikanath, and Joachim M. Buhmann. "Cardiac LV and RV segmentation using mutual context information." International Workshop on Machine Learning in Medical Imaging. Springer Berlin Heidelberg, 2012.*

Lin, Xiang, Brett Cowan, and Alistair Young. "Model-based graph cut method for segmentation of the left ventricle." Engineering in Medicine and Biology Society, 2005. IEEE-EMBS 2005. 27th Annual International Conference of the. IEEE, 2006.*

H. A. Kirisli et al., "Fully automatic cardiac segmentation from 3D CTA data: a multi-atlas based approach", Proc. SPIE, vol. 7623, Medical Imaging 2010: Image Processing, pp. 762305-1-762305-9, Mar. 2010.

J. Ulén et al., "Optimization for Multi-Region Segmentation of Cardiac MRI", STACOM'11 Proceedings of the Second International Workshop on Statistical Atlases and Computational Models of the Heart: Imaging and Modelling Challenges, pp. 1-10, Apr. 2011.

Y. Zheng at al., "Four-Chamber Heart Modeling and Automatic Segmentation for 3D Cardiac CT Volumes Using Marginal Space Learning and Steerable Features", IEEE Transactions on Medical Imaging, vol. 27, No. 11, pp. 1-14, Aug. 2008.

M. Etoh, "Survey of Snakes, Active Contour Models", Medical Imaging Technology, vol. 12, No. 1, pp. 9-15, Jan. 1994, and a partial English translation thereof.

M. Kass et al., "Snakes: Active Contour Models", International Journal of Computer Vision, vol. 1, pp. 321-331, Jan. 1988.

"Office Action of Japan Counterpart Application" with machine English translation, dated Jul. 5, 2016, p. 1-p. 5.

* cited by examiner

MEDICAL IMAGE PROCESSING APPARATUS, METHOD, AND PROGRAM

CROSS-REFERENCE TO RELATED APPLICATIONS

This application is a Continuation of PCT International Application No. PCT/JP2014/000076 filed on Jan. 10, 2014, which claims priority under 35 U.S.C. § 119 (a) to Japanese Patent Application No. 2013-005050 filed on Jan. 16, 2013. Each of the above application(s) is hereby expressly incorporated by reference, in its entirety, into the present application.

BACKGROUND

The present invention relates to a medical image processing apparatus, method, and program for extracting a left ventricular region, a right ventricular region, and the like from medical image data containing an image of a heart.

Heretofore, various methods have been proposed for extracting, for example, a left ventricular region of a heart from a medical image, such as a computed tomography (CT) image, a magnetic resonance imaging (MRI) image, or an ultrasound image (refer to H. A. Kirisli et al., "Fully automatic cardiac segmentation from 3D CTA data: a multi-atlas based approach", Proc. SPIE, Vol. 7623, Medical Imaging 2010: Image Processing, pp. 762305-1-762305-9, 2010, J. Ulén et al., "Optimization for Multi-Region Segmentation of Cardiac MRI", STACOM'11 Proceedings of the Second International Workshop on Statistical Atlases and Computational Models of the Heart: Imaging and Modelling Challenges, pp. 1-10, 2011, and Y. Zheng et al., "Four-Chamber Heart Modeling and Automatic Segmentation for 3D Cardiac CT Volumes Using Marginal Space Learning and Steerable Features", IEEE Transactions on Medical Imaging, Vol. 27, No. 11, pp. 1-14, 2008).

Further, four-dimensional medical images in which a time axis is added to the spatial three-dimensions have become obtainable in recent years, and more specifically, a plurality of three-dimensional medical images has become obtainable during one heartbeat. Analyzing a plurality of such cardiac three-dimensional images allows further analysis of cardiac functions, including ejection fraction, end-diastolic volume, end-systolic volume, stroke volume, cardiac output, and cardiac mass.

A heart has four rooms, and the automatic extraction of a left ventricle, which is supposed to be clinically the most important, has been most intensively studied, but now the right ventricle, and left and right atriums have also become the subject of research. Improving the accuracy of automatic extraction of these rooms will be able to reduce the work burden on the doctors for correction.

SUMMARY

Here, H. A. Kirisli et al., "Fully automatic cardiac segmentation from 3D CIA data: a multi-atlas based approach", Proc. SPIE, Vol. 7623, Medical Imaging 2010: Image Processing, pp. 762305-1-762305-9, 2010 and J. Ulén et al., "Optimization for Multi-Region Segmentation of Cardiac MRI", STACOM'11 Proceedings of the Second International Workshop on Statistical Atlases and Computational Models of the Heart: Imaging and Modelling Challenges, pp. 1-10, 2011 propose a method for extracting a plurality of rooms of a heart simultaneously.

As the shape of each room of the heart varies from person to person, however, the combination patterns amount to a huge number. Therefore, it is necessary to cope with the huge variations to extract a plurality of rooms simultaneously as in the methods described in H. A. Kirisli et al., "Fully automatic cardiac segmentation from 3D CTA data: a multi-atlas based approach", Proc. SPIE, Vol. 7623, Medical Imaging 2010: Image Processing, pp. 762305-1-762305-9, 2010 and J. Ulén et al., "Optimization for Multi-Region Segmentation of Cardiac MRI", STACOM'11 Proceedings of the Second International Workshop on Statistical Atlases and Computational Models of the Heart: Imaging and Modelling Challenges, pp. 1-10, 2011, but because it is difficult to represent such a huge number of combination patterns, it is difficult to simultaneously extract each room with high accuracy. In particular, the use of shape models which use an atlas image or a training image as in principal component models, such as active shape model, causes a difficulty in getting accuracy.

Y. Zheng et al., "Four-Chamber Heart Modeling and Automatic Segmentation for 3D Cardiac CT Volumes Using Marginal Space Learning and Steerable Features", IEEE Transactions on Medical Imaging Vol. 27, No. 11, pp. 1-14, 2008 extracts each room individually and reduces the number of variations in comparison with the case where each room is extracted simultaneously from the entire heart.

The accuracy is likely to be obtained by reducing the number of variations to be coped with through individual room extraction processing, but if an extraction error occurs in the individual processing, a problem arises that mismatching occurs in the extraction results of each room.

In view of the circumstances described above, it is an object of the present invention to provide a medical image processing apparatus, method, and program capable of extracting each region corresponding to each room of a heart with high accuracy.

A medical image processing apparatus of the present invention includes a medical image data obtaining unit for obtaining medical image data containing an image of a heart, and a region extraction processing unit for extracting a left ventricular region of the heart in the medical image data obtained by the medical image data obtaining unit, and, based on an extraction result of the left ventricular region, performing region extraction processing for extracting at least one of a right ventricular region, a left atrium region, and a right atrium region of the heart.

The medical image processing apparatus of the present invention described above may be configured such that the region extraction processing unit limits pixels of the medical image data for a target of the region extraction processing based on the extraction result of the left ventricular region.

Further, the region extraction processing unit may be configured to set an evaluation function based on the extraction result of the left ventricular region and to perform the region extraction processing by finding an optimal solution of the evaluation function.

Still further, the region extraction processing unit may be configured to extract the right ventricular region based on the extraction result of the left ventricular region, and then extracts the right atrium region or the left atrium region.

Further, the medical image data obtaining unit may be configured to obtain a plurality of medical image data in different phases of one cardiac cycle of the heart which is beating, and the region extraction processing unit may be configured to extract a left ventricular region in medical image data of one medical image in diastole of the plurality of medical image data, then to extract, based on the extraction result of the left ventricular region, at least one of a right ventricular region, a left atrium region, and a right atrium region in the medical image data of one medical image in diastole, and to extract, based on the extraction result of the medical image data of one medical image in diastole, at least one of a right ventricular region, a left atrium region, and a right atrium region in medical image data in a phase other than that of the medical image data of one medical image in diastole.

Still further, the region extraction processing unit may be configured to extract a left ventricular region in medical image data of one medical image in end-diastole of the plurality of medical image data, then to extract, based on the extraction result of the left ventricular region, at least one of the right ventricular region, the left atrium region, and the right atrium region in the medical image data of one medical image in end-diastole, and to extract, based on the extraction result of the medical image data of one medical image in end-diastole, at least one of the right ventricular region, the left atrium region, and the right atrium region in medical image data in the phase other than that of the medical image data of one medical image in end-diastole.

Further, the region extraction processing unit may be configured to receive, if there is an anomaly in the extraction result of each region in the medical image data of one medical image in diastole, a manual correction of a contour point of the region having the anomaly and to perform the region extraction processing again for the medical image data in a phase other than that of the medical image data of one medical image in diastole based on the corrected contour point.

Still further, the region extraction processing unit may be configured to detect a plurality of landmarks in the medical image data and to extract the left ventricular region based on a detection result of the landmarks detected.

Further, the region extraction processing unit may be configured to receive, if the left ventricular region or the at least one region has not been extracted based on the extraction result of the plurality of landmarks, or if there is an anomaly in the left ventricular region or the at least one region extracted, a manual correction of the landmarks and to perform the region extraction processing again based on the corrected landmarks.

Still further, the region extraction processing unit may be configured to receive, if the extracted left ventricular region is abnormal, a manual correction of a contour point of the left ventricular region and to perform the region extraction processing again for the left ventricular region based on the corrected contour point.

Further, three-dimensional image data may be used as the medical image data.

A medical image processing method of the present invention includes the steps of obtaining medical image data containing an image of a heart, extracting a left ventricular region of the heart in the medical image data obtained, and, based on an extraction result of the left ventricular region, extracting at least one of a right ventricular region, a left atrium region, and a right atrium region.

A medical image processing program of the present invention causes a computer to function as a medical image data obtaining unit for obtaining medical image data containing an image of a heart, and a region extraction processing unit for extracting a left ventricular region of the heart in the medical image data obtained by the medical image data obtaining unit and, based on an extraction result of the left ventricular region, performing region extraction processing for extracting at least one of a right ventricular region, a left atrium region, and a right atrium region of the heart.

According to the medical image processing apparatus, method, and program of the present invention, medical image data containing an image of a heart are obtained, then a left ventricular region of the heart in the medical image data obtained is extracted, and based on an extraction result of the left ventricular region, at least one of a right ventricular region, a left atrium region, and a right atrium region of the heart is extracted. This allows each region of the heart to be extracted with high accuracy.

That is, the left ventricular region of the heart has a relatively simple shape and is capable of being extracted with high accuracy through independent extraction. Then, using the extraction result of the left ventricular region as reliable information, other regions are extracted, whereby extraction accuracy of the other regions may be improved and extraction errors may be reduced.

DETAILED DESCRIPTION OF THE PREFERRED EMBODIMENTS

Figure 1:
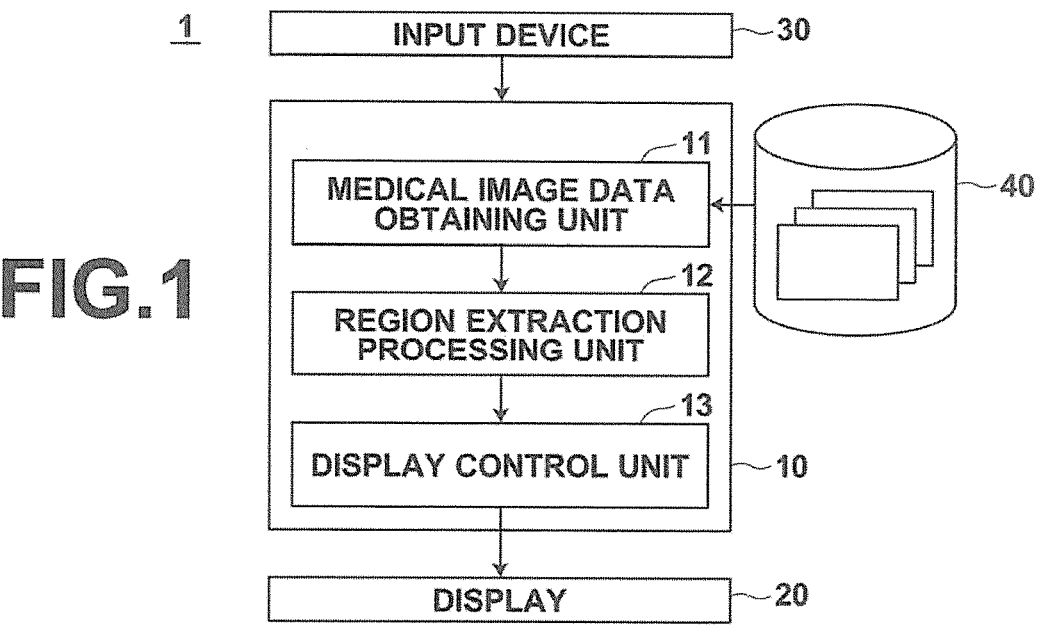
FIG. 1 is a block diagram of a medical image diagnosis support system that uses one embodiment of the medical image processing apparatus, method, and program of the present invention, illustrating a schematic configuration thereof.

Hereinafter, a medical image diagnosis support system that uses one embodiment of the medical image processing apparatus, method, and program of the present invention will be described in detail with reference to the accompanying drawings. FIG. 1 is a block diagram of the medical image diagnosis support system that uses the present embodiment, illustrating a schematic configuration thereof.

As illustrated in FIG. 1, the medical image diagnosis support system 1 of the present embodiment includes a medical image processing apparatus 10, a display 20, an input device 30, and a medical image data storage server 40.

The medical image processing apparatus 10 is configured by installing a medical image processing program of the present embodiment on a computer. The medical image processing apparatus 10 includes a central processing unit (CPU) and storage devices, such as for example, a semi-conductor memory, a hard disk on which the medical image processing program of the present embodiment is installed, and a solid state drive (SSD). These pieces of hardware constitutes a medical image data obtaining unit 11, a region extraction processing unit 12, and a display control unit 13. Then, each unit operates when the medical image processing program installed on the hard disk is executed by the central processing unit.

The medical image data obtaining unit 11 obtains medical image data containing an image of a heart captured in advance. The medical image data may be tomographic image data outputted, for example, from a CT system, a MRI system, a Multi slice (MS) CT system, a cone beam CT system, or an ultrasound imaging system, and volume data reconstructed from the tomographic image data. The medical image data are stored in the medical image data storage server 40 in advance with subject identification information, and the medical image data obtaining unit 11 reads out medical image data corresponding to the subject identification information inputted at the input device 30 from the medical image data storage server 40.

The region extraction processing unit 12 performs region extraction processing using a graph cut method on the medical image data obtained by the medical image data obtaining unit 11. The region extraction processing unit 12 extracts a left ventricular region of a heart in the medical image data by performing the region extraction processing, then based on an extraction result of the left ventricular region, extracts at least one of a right ventricular region, a left atrium region, and a right atrium region of the heart. In the present embodiment, it is assumed that the right ventricular region is extracted, then the left atrium region and the right atrium region are extracted in this order, after extracting the left ventricular region. A specific method for extracting these regions will be described in detail later.

The display control unit 13 displays tomographic image data obtained by the medical image data obtaining unit 11 and a voxel model or a surface model obtained by performing volume rendering or surface rendering on the volume data on the display 20.

The display control unit 13 also receives an extraction result of each region in the region extraction processing unit 12 and, based on the extraction result, displays an image with each region being color coded. Present embodiment displays the color coded image superimposed on the tomographic image, the voxel model, or the surface model.

The input device 30 receives a user input of given information and is composed, for example, of a pointing device, such as a keyboard, a mouse, or the like.

Figure 2:
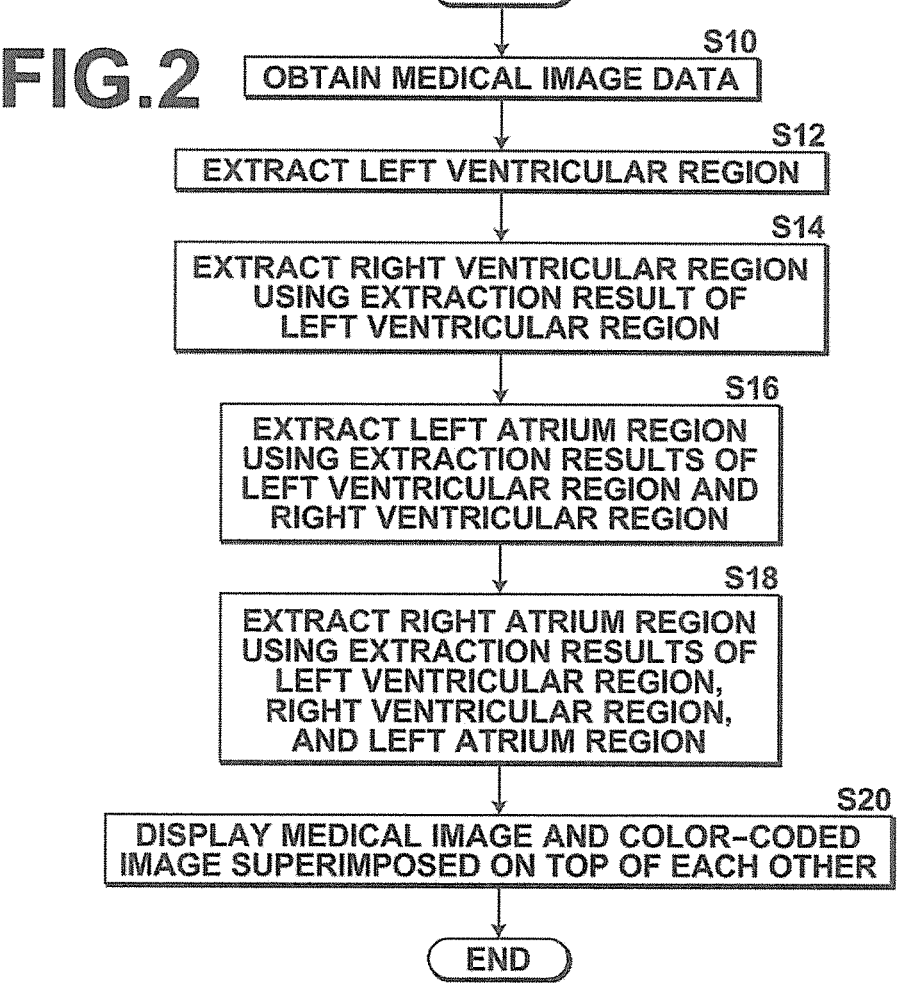
FIG. 2 is a flowchart for explaining an operation of the medical image diagnosis support system that uses one embodiment of the medical image processing apparatus, method, and program of the present invention.

Next, an operation of the medical image diagnosis support system that uses one embodiment of the present invention will be described with reference to the flowchart shown in FIG. 2.

First, subject identification information is inputted at the input device 30 and the medical image data obtaining unit 11 of the medical image processing apparatus 10 reads out and obtains medical image data corresponding to the inputted subject identification information from the medical image data storage server 40 (S10). It is assumed here that medical image data captured by a CT system are read out and obtained as the medical image data.

Figure 3:
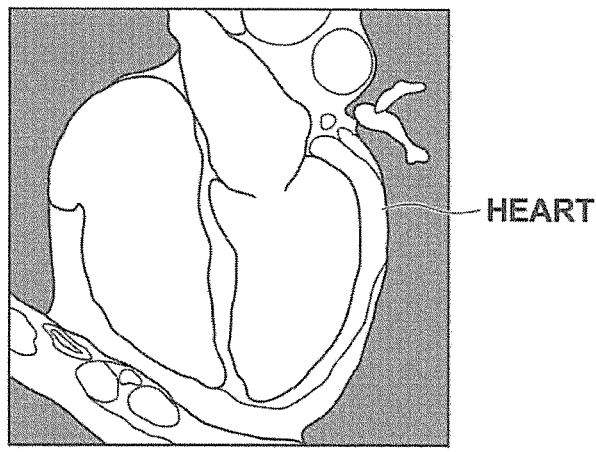
FIG. 3 illustrates an example of medical image data containing an image of a heart.
Figure 4:
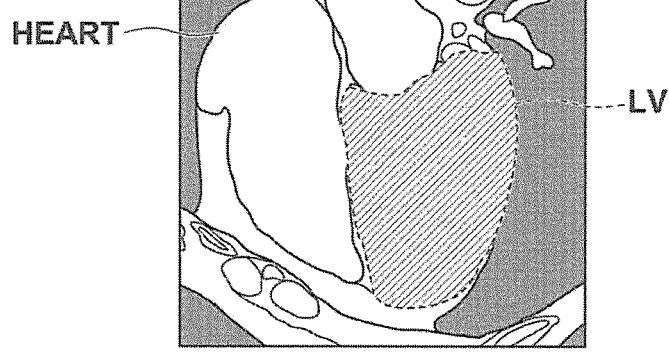
FIG. 4 illustrates a left ventricular region LV of the heart in the medical image data shown in FIG. 3.

The medical image data obtained by the medical image data obtaining unit 11 are inputted to the region extraction processing unit 12 and the region extraction processing unit 12 extracts a left ventricular region of a heart in the medical image data first by performing region extraction processing on the inputted medical image data (S12). FIG. 3 illustrates an example of medical image data containing an image of a heart obtained by the medical image data obtaining unit 11. FIG. 4 illustrates a left ventricular region LV of the heart in the medical image data shown in FIG. 3.

Figure 5:
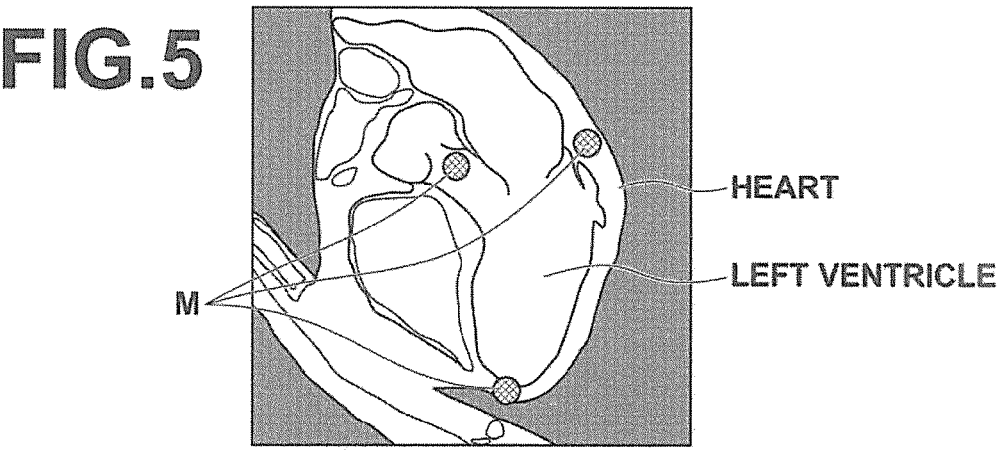
FIG. 5 illustrates an example of a plurality of landmarks M in the medical image data.

More specifically, a plurality of landmarks M is specified and set-inputted by the user using the input device 30, as illustrated in FIG. 5. It is preferable that, for the number of landmarks M, at least three points are set-inputted, as shown in FIG. 5. For the positions of the landmarks, the positions of the mitral valve and aortic valve in the left ventricular region of the heart and the position of the apex of the left ventricular region are specified, and set-inputted. In the present embodiment, the landmarks M are set-inputted by the user, but not limited to this, and the positions of the mitral valve, aortic valve, and apex of the left ventricular region may be automatically extracted using pattern matching.

Since the present embodiment uses landmarks also in extracting a right ventricular region, a left atrium region, and a right atrium region, as will be described later in detail, five landmarks M shown in FIG. 6 will actually be set. As for the additional two points, for example, the positions of the tricuspid valve, cardiac base located adjacent to the entrance of the aorta and the superior vena cava are automatically or manually set.

Then, based on the position information of the landmarks set-inputted by the user or automatically extracted, the region extraction processing unit 12 sets an initial region of the left ventricular region. The initial region of the left ventricular region refers to a region of roughly extracted left ventricular region. Various known methods may be used for the method of extracting the initial region using the landmarks M. The left ventricular region has a conical shape which is a simpler shape in comparison with those of the other regions of right ventricular region, left and right atrium regions, and is capable of being extracted with high accuracy. As for the method of extracting the left ventricular region, the method described in Y. Zheng et al., "Four-Chamber Heart Modeling and Automatic Segmentation for 3D Cardiac CT Volumes Using Marginal Space Learning and Steerable Features", IEEE Transactions on Medical Imaging, Vol. 27, No. 11, pp. 1-14, 2008 may be used.

Further, the initial region of the left ventricular region may be set using atlas image data which include an image of the heart. The atlas image data are, for example, those generated by a doctor or the like using a general anatomical chart and represents a typical heart shape.

Figure 6:
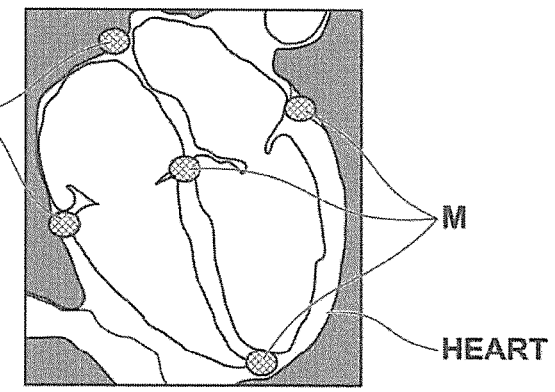
FIG. 6 illustrates an example of a plurality of landmarks M in the medical image data.

More specifically, using landmarks in the atlas image data automatically set or manually set-inputted and the landmarks M shown in FIG. 6 set-inputted in the extraction target medical image data, the region extraction processing unit 12 performs a rough registration between these image data. The landmarks in the atlas image data are set automatically or manually as landmarks corresponding to the landmarks M shown in FIG. 6.

Then, after the foregoing rough registration, the region extraction processing unit 12 performs a non-rigid registration to obtain a corresponding relationship between the pixels of the two sets of image data as a matching function. Then, using the matching function, the region extraction processing unit 12 obtains a region in the medical image data corresponding to the left ventricular region which is the correct region in the atlas image data and sets the region as an initial region of the left ventricular region.

Then, using pixels in the initial region of the left ventricular region extracted in the manner described above and pixels in an area surrounding the initial region as the extraction processing target pixels, the region extraction processing unit 12 generates a graphical model in the graph cut method. Then, the region extraction processing unit 12 performs region extraction processing using the graph cut method to extract the final left ventricular region. Hereinafter, the region extraction processing using the graph cut method will be described.

Figure 7:
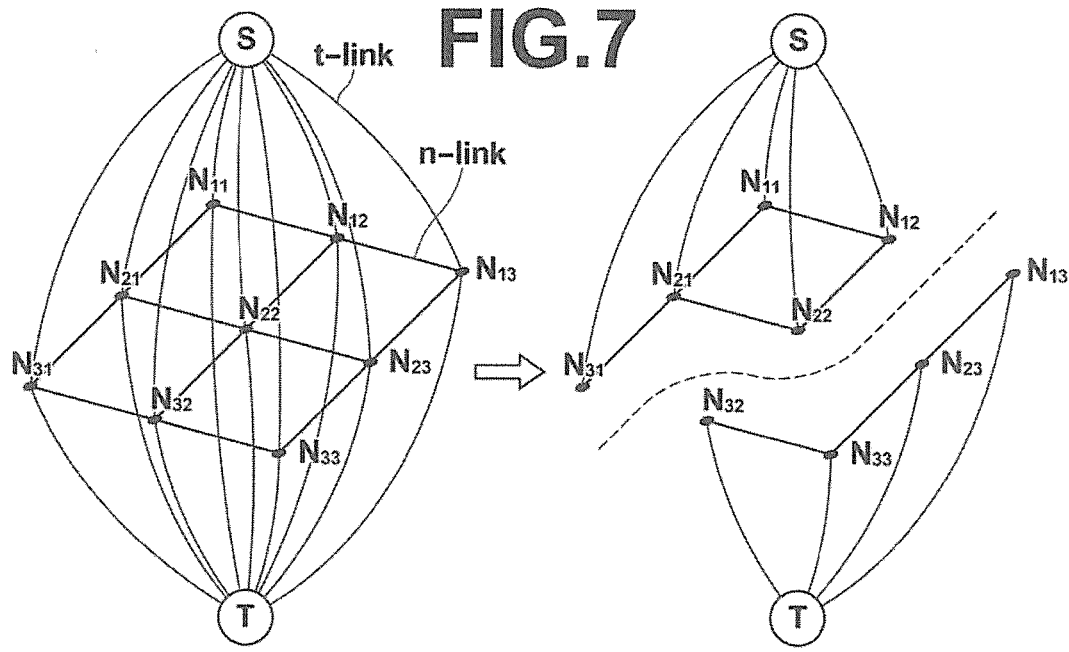
FIG. 7 is a drawing for explaining region extraction processing using a graph cut method.

More specifically, the region extraction processing unit 12 generates a graphical model composed of a node $N_{ijk}$ representing each of the processing target pixels described above, nodes S, T representing labels which can be taken by each pixel (left ventricular region and a region other than the left ventricular region, here), an n-link which is a link connecting the nodes of adjacent pixels, and a t-link which is a link connecting the node $N_{ijk}$ representing each pixel to the node S representing the left ventricular region or the node T representing a region other than the left ventricular region (refer to the left drawing in FIG. 7. Note that, however, FIG. 7 shows the segmentation of two-dimensional region for facilitating understanding).

Here, the n-link represents a likelihood that the adjacent pixels are voxels in the same region and the likelihood may be obtained, for example, based on the difference in pixel value between the adjacent pixels. The t-link connecting the node $N_{ijk}$ representing each pixel to the node T representing a region other than the left ventricular region represents a likelihood that the pixel is a pixel included in a surrounding region other than the left ventricular region. The t-link connecting the node $N_{ijk}$ representing each pixel to the node S representing the left ventricular region represents a likelihood that the pixel is a pixel included in the left ventricular region.

The n-link and the t-link described above may be expressed as a cost function representing likelihood.

Then, as the left ventricular region, the present embodiment separately extracts a contrast region and a myocardial region constituting the left ventricular region.

Therefore, when extracting the contrast region, the t-link connecting the node $N_{ijk}$ to the node T representing a region other than the contrast region may be calculated, for example, based on a judgment result as to whether or not the pixel value is in the range of CT values in the surrounding region of the contrast region statistically obtained in advance. Further, the t-link connecting the node $N_{ijk}$ to the node S representing the contrast region may be calculated, for example, based on a judgment result as to whether or not the pixel value is in the range of CT values in the contrast region statistically obtained in advance.

Then, one of the two t-links connecting the node representing each pixel to the node S representing the contrast region or the node T representing a region other than the contrast region is cut off and an n-link connecting nodes of adjacent pixels having different labels is cut off, whereby the graphical model is segmented into the contrast region and a region other than the contrast region (refer to the right drawing in FIG. 7). Here, minimizing the sum of the costs of all the t-links and n-links to be cut off allows an optimum region segmentation. That is, when the cost function of the t-link is taken as fv(Xv) and the cost function of the n-link is taken as fuv(Xu, Xv), the region segmentation is performed such that the sum E(x) of the costs in the formula given below is minimized.

$$E(X) = \sum_{v \in V} f_v(X_v) + \sum_{(u,v) \in \mathcal{E}} f_{uv}(X_u, X_v) \qquad \text{[Formula 1]}$$

When extracting the myocardial region, the t-link connecting the node $N_{ijk}$ to the node T representing a region other than the myocardial region may be calculated, for example, based on a judgment result as to whether or not the pixel value is in the range of CT values in the surrounding region of the myocardial region statistically obtained in advance. Further, the t-link connecting the node $N_{ijk}$ to the node S representing the myocardial region may be calculated, for example, based on a judgment result as to whether or not the pixel value is in the range of CT values in the myocardial region statistically obtained in advance.

Then, one of the two t-links connecting the node representing each pixel to the node S representing the myocardial region or the node T representing a region other than the myocardial region is cut off and an n-link connecting nodes of adjacent pixels having different labels is cut off, whereby the graphical model is segmented into the myocardial region and a region other than the myocardial region. Here, minimizing the sum of the costs of all the t-links and n-links to be cut off, i.e., finding the optimum solution, allows an appropriate region segmentation.

The region extraction processing unit 12 extracts the contrast region and the myocardial region by the graph cut method in the manner described above, thereby obtaining the final left ventricular region LV that combines these regions.

Next, the region extraction processing unit 12 extracts a right ventricular region of the heart based on the foregoing extraction result of the left ventricular region (S14).

First, the region extraction processing unit 12 sets an initial region of the right ventricular region using the atlas image data which include an image of the heart, as in the extraction of the left ventricular region.

Next, using pixels in the initial region of the right ventricular region extracted in the manner described above and pixels in an area surrounding the initial region as the extraction processing target pixels, the region extraction processing unit 12 generates a graphical model in the graph cut method. Then, the region extraction processing unit 12 performs region extraction processing using the graph cut method to extract the final right ventricular region RV. Here, the region extraction processing unit 12 performs the region extraction processing using the extraction result of the left ventricular region.

More specifically, the region extraction processing unit 12 sets the foregoing cost function fv(Xv) (corresponding to the evaluation function) such that a relatively large cost is allocated to a pixel extracted as the left ventricular region LV, thereby preventing the pixel extracted as the left ventricular region from being extracted as a pixel of the right ventricular region. Note that the content of the region extraction processing by the graph cut method is identical to that of the region extraction processing for the left ventricular region described above other than the way of setting the cost function fv(Xv) described above.

In the foregoing description, the cost function for a pixel extracted as the left ventricular region is controlled, as the method of using the extraction result of the left ventricular region, but the method is not limited to this and, for example, a graphical mode may be generated by excluding the pixels extracted as the left ventricular region when generating the foregoing graphical model.

Next, the region extraction processing unit 12 extracts a left atrium region of the heart based on the extraction results of the left ventricular region and the right ventricular region described above (S16).

The region extraction processing unit 12 sets an initial region of the left atrium region using the atlas image data, as in the extraction of the right ventricular region.

Next, using pixels in the initial region of the left atrium region extracted in the manner described above and pixels in an area surrounding the initial region as the extraction processing target pixels, the region extraction processing unit 12 generates a graphical model in the graph cut method. Then, the region extraction processing unit 12 performs region extraction processing using the graph cut method to extract the final left atrium region. Here, the region extraction processing unit 12 performs the region extraction processing using the extraction results of the left ventricular region and the right ventricular region.

More specifically, the region extraction processing unit 12 sets the foregoing cost function fv(Xv) such that a relatively large cost is allocated to the pixels extracted as the left ventricular region and the right ventricular region, thereby preventing pixels extracted as the left ventricular region and the right ventricular region from being extracted as pixels of the left atrium region. Note that the content of the region extraction processing by the graph cut method is identical to the foregoing region extraction processing other than the way of setting the cost function fv(Xv) described above.

Also, in extracting the left atrium region, when generating a graphical model, the graphical model may be generated by excluding the pixels extracted as the left ventricular region and the right ventricular region.

Next, the region extraction processing unit 12 extracts a right atrium region of the heart based on the extraction results of the left ventricular region, the right ventricular region, and the left atrium region described above (S18).

The region extraction processing unit 12 sets an initial region of the right atrium region using the atlas image data, as in the extraction of the right ventricular region.

Next, using pixels in the initial region of the right atrium region extracted in the manner described above and pixels in an area surrounding the initial region as the extraction processing target pixels, the region extraction processing unit 12 generates a graphical model in the graph cut method. Then, the region extraction processing unit 12 performs region extraction processing using the graph cut method to extract the final right atrium region. Here, the region extraction processing unit 12 performs the region extraction processing using the extraction results of the left ventricular region, the right ventricular region, and the left atrium region.

More specifically, the region extraction processing unit 12 sets the foregoing cost function fv(Xv) such that a relatively large cost is allocated to the pixels extracted as the left ventricular region, the right ventricular region, and the left atrium region, thereby preventing the pixels extracted as the left ventricular region, the right ventricular region, and the left atrium region from being extracted as pixels of the right atrium region. Note that the content of the region extraction processing by the graph cut method is identical to the foregoing region extraction processing other than the way of setting the cost function fv(Xv) described above.

Also, in extracting the right atrium region, when generating a graphical model, the graphical model may be generated by excluding the pixels extracted as the left ventricular region, the right ventricular region, and the left atrium region.

The region extraction processing unit 12 extracts the left ventricular region, the right ventricular region, the left atrium region, and the right atrium region in this order in the manner described above. Then, region extraction processing unit 12 outputs the extraction results to the display control unit 13.

Figure 8:
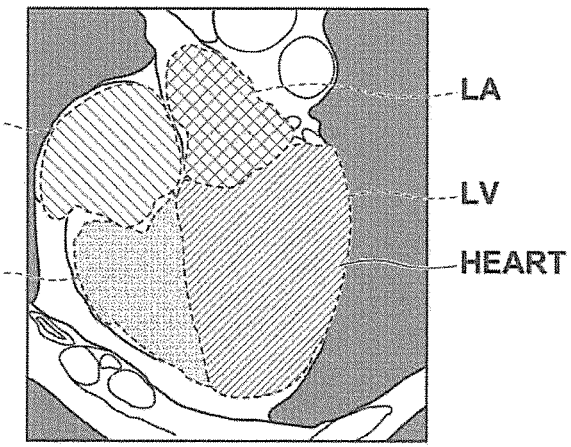
FIG. 8 illustrates an example of a left ventricular region LV, a right ventricular region RV, a left atrium region LA, and a right atrium region RA.

Based on the inputted extraction results, the display control unit 13 generates an image with the respective regions of the left ventricular region LV, the right ventricular region RV, the left atrium region LA, and the right atrium region RA being color-coded, as illustrated in FIG. 8, and displays the generated color-coded image on the display 20 superimposed on the medical image.

According to the medical image diagnosis support system 1 of the foregoing embodiment, medical image data containing an image of a heart is obtained, then the left ventricular region of the heart is independently extracted, and, based on the extraction result of the left ventricular region, at least one of the right ventricular region, the left atrium region, and the right atrium region is extracted. This allows each region of the heart to be extracted with high accuracy.

That is, the left ventricular region of a heart has a relatively simple shape and is capable of being extracted with high accuracy through independent extraction. Then, using the extraction result of the left ventricular region as reliable information, other regions are extracted, whereby extraction accuracy of the other regions may be improved and extraction errors may be reduced.

As described above, the present embodiment first extracts the left ventricular region and then the right ventricular region. The right ventricular region is a region that shares the border with the left ventricular region to the largest extent. Therefore, the use of the extraction result of the left ventricular region may prevent over extraction to the side of the left ventricular region or insufficient extraction of the right ventricular region effectively.

The foregoing embodiment extracts, of the left atrium region and the right atrium region, the left atrium region first, after extracting the right ventricular region, but the right atrium region may be extracted first. In this case, the extraction results of the left ventricular region and the right ventricular region may be used when extracting the right atrium region, and the extraction results of the left ventricular region, the right ventricular region, and the right atrium region may be used when extracting the left atrium region.

Further, the foregoing embodiment performs region extraction processing by the graph cut method when extracting the right ventricular region using the extraction result of the left ventricular region, but the region extraction processing is not limited to this. For example, region extraction processing may be performed using the atlas image data used when extracting the initial region in the foregoing description to extract the final right ventricular region.

Figure 9:
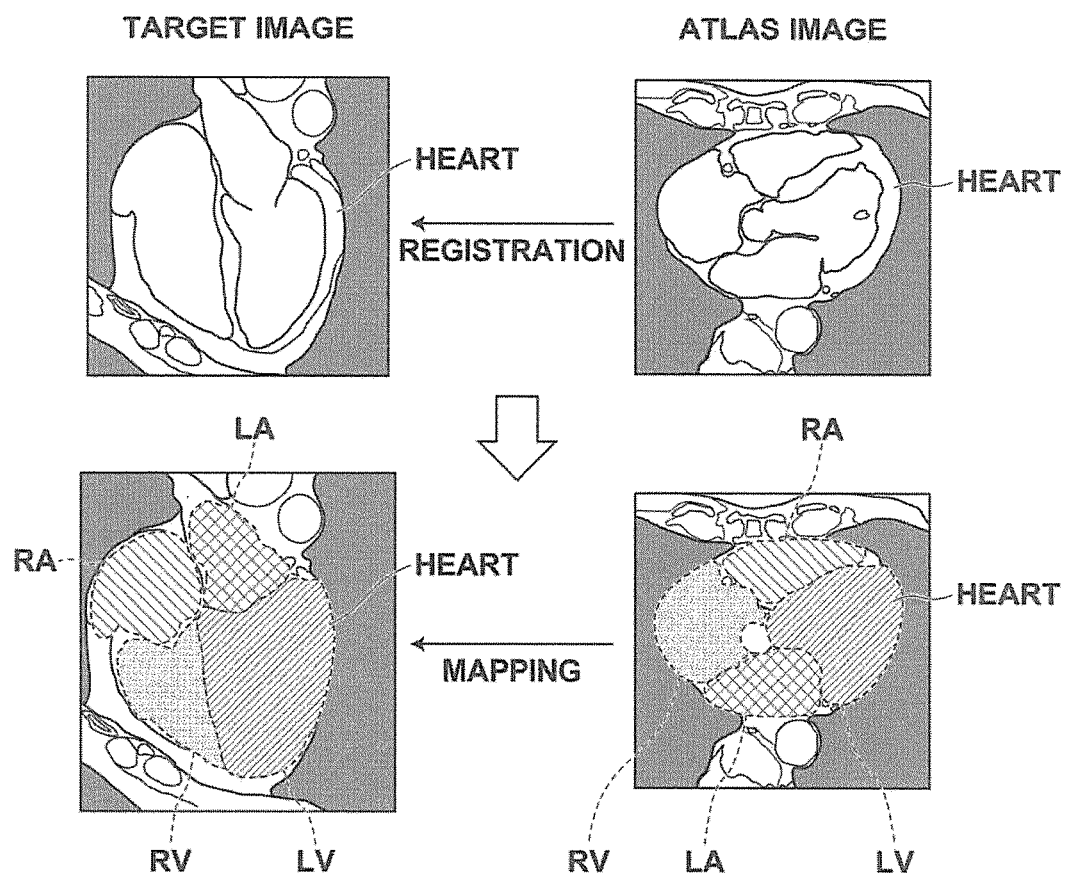
FIG. 9 is a drawing for explaining region extraction processing using an atlas image.

More specifically, a non-rigid registration is performed between the atlas image data and extraction target medical image data to obtain a corresponding relationship between the pixels of the two sets of image data as a matching function, as illustrated in FIG. 9. This time, the pixels extracted as the left ventricular region are excluded from the target pixels for obtaining the matching function.

Then, a region in the medical image data corresponding to the right ventricular region RV, which is the correct region in the atlas image data, is obtained using the matching function obtained in the manner described above, and the obtained region is extracted as the final right ventricular region RV.

Further, region extraction processing using the atlas image data may also be performed when extracting the left atrium region and the right atrium region in the same manner as described above. In this case, the pixels extracted as the left ventricular region and the right ventricular region may be excluded from the target pixels for obtaining the matching function when extracting the left atrium region and the pixels extracted as the left ventricular region, the right ventricular region, and the left atrium region may be excluded from the target pixels for obtaining the matching function when extracting the right atrium region.

When extracting the right ventricular region using the extraction result of the left ventricular region, region extraction processing using an active contour model may be performed other than the region extraction processing using the atlas image data described above. The region extraction processing using an active contour model defines an evaluation function and finds an optimal solution by calculating the evaluation function while changing the position of a contour point of the extraction target region. The region extraction processing using an active model is a known method and, for example, the method described in M. Etoh, "Survey of Snakes, Active Contour Models", Medical Imaging Technology, Vol. 12, No. 1, pp. 9-15, 1994 and the method described in M. Kass et al., "Snakes: Active Contour Models", International Journal of Computer Vision, Vol. 1, pp. 321-331, 1988 may be used. The evaluation function is defined by three terms with respect to $v(s)=(x(s), y(s))$, as shown in a formula given below:

$$E=E_{int}(v(s))+E_{image}(v(s))E_{con}(v(s)).\quad\quad\text{[Formula 2]}$$

Note that, "Eint" is a term representing internal energy and controls the smoothness of the contour. The "Eimage" is a term representing image energy and controls the position of the contour to a position having a large luminance change. The "Econ" is a term representing external energy and in a case, for example, where a portion of the contour is desired to be fixed by the specification from outside, a term $(v(s)-p)^2$ of difference between the point on the contour $v(s)$ and the specified point p may be added.

Then, when performing region extraction processing of the right ventricular region using the extraction result of the left ventricular region, a penalty term that lowers the evaluation value when a contour point enters into the left ventricular region may be provided, as the Econ representing external energy. This may suppress extraction errors.

Further, region extraction processing using the active contour model may also be performed when extracting the left atrium region and the right atrium region in the same manner as described above. In this case, a penalty term that lowers the evaluation value when a contour point enters into the left ventricular region or the right ventricular region may be provided, as the Econ representing external energy, when extracting the left atrium region, and a penalty term that lowers the evaluation value when a contour point enters into the left ventricular region, the right ventricular region, or the left atrium region may be provided, as the Econ representing external energy, when extracting the right atrium region.

The foregoing embodiment may be configured such that a plurality of medical image data in different phases of one cardiac cycle of a beating heart is obtained by the medical image data obtaining unit 11, and left and right ventricular regions and left and right atrium regions are extracted from the plurality of medical image data.

Figure 10:
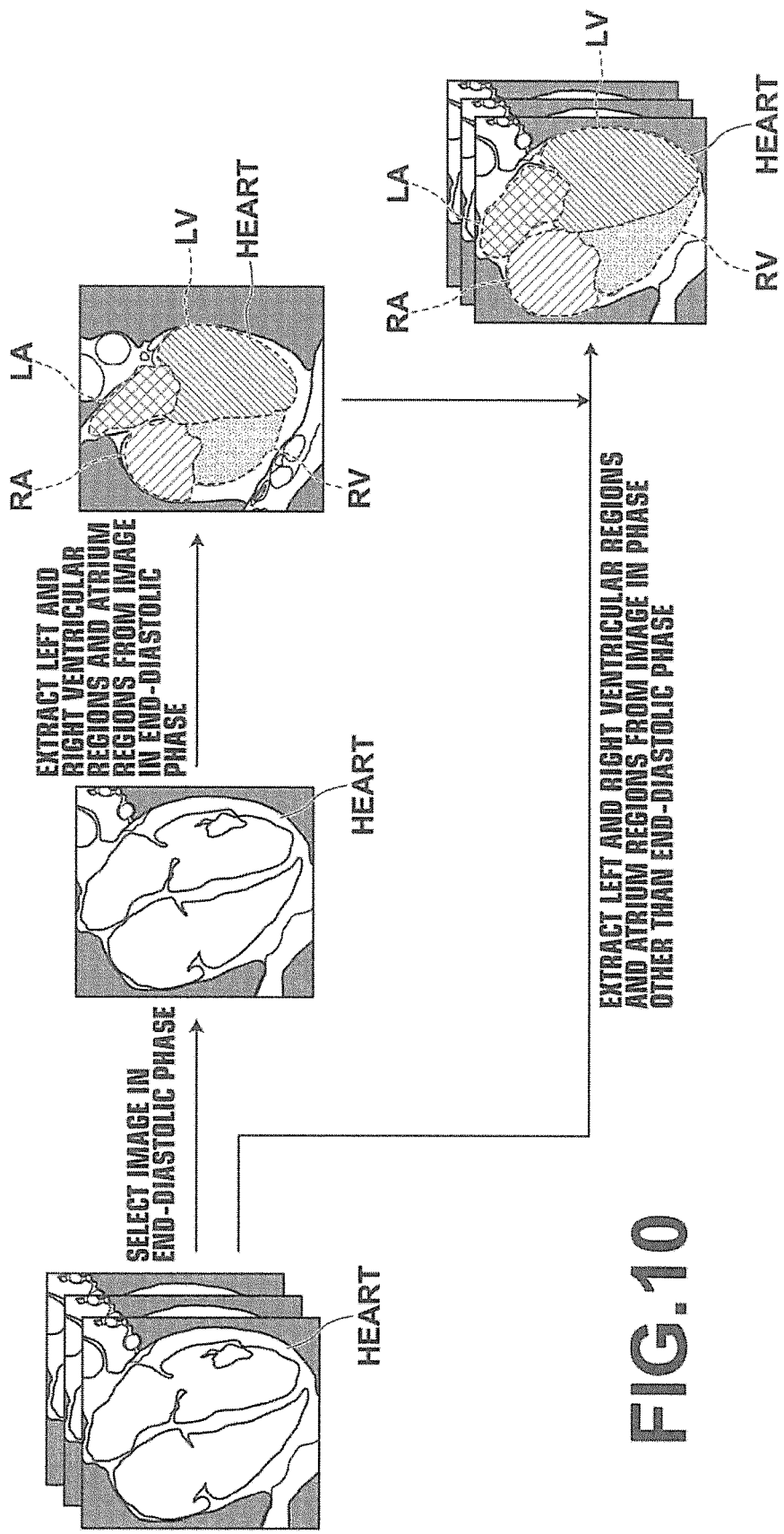
FIG. 10 is a drawing for explaining a method of performing region extraction processing, using an extraction result of medical image data of one medical image in diastolic phase, on medical image data in a phase other than that of the medical image data of one medical image.

In that case, medical image data of one medical image in diastole is selected first from the plurality of medical image data in different phases, as illustrated in FIG. 10. More specifically, image data in end-diastolic phase is preferably selected. The medical image data in end-diastolic phase can be said to be medical image data more suitable for region extraction in that the movement is small and the shape is stable. But, not limited to the medical image data in end-diastolic phase, and medical image data in the other phase of diastole may be used.

Then, the left ventricular region LV is extracted first by the same method as described above based on the selected medical image data in end-diastolic phase. Next, the right ventricular region RV, the left atrium region LA, and right atrium region RA in the medical image in end-diastolic phase are extracted by the same method as described above using the extraction result of the left ventricular region LV.

Next, based on the extraction result of the medical image data in end-diastolic phase, left and right ventricular regions LV, RV, and left and right atrium regions LA, RA of medial image data in a phase other than that of the medical image data of one medical image are extracted.

More specifically, a non-rigid registration is performed between the medical image data in the end-diastole and medical image data in a phase other than that phase to obtain a corresponding relationship between the pixels of the two sets of image data as a matching function.

Then, regions in the medical image data in a phase other than that of the medical image data of one medical image corresponding to the left and right ventricular regions LV, RV and the left and right atrium regions in the medical image data of one medical image are obtained using the matching function obtained in the manner described above, and the obtained regions are extracted as the left and right ventricular regions LV, RV and the left and right atrium regions LA, RA.

Note that the method of extracting the left and right ventricular regions LV, RV and the left and right atrium regions LA, RA of the image data in a phase other than that of the medical image data in end-diastolic phase is not limited to the foregoing method, and, for example, the extraction results of the left and right ventricular regions LV, RV and the left and right atrium regions LA, RA of the medical image data in end-diastolic phase may be set as initial regions of the left and right ventricular regions LV, RV and the left and right atrium regions LA, RA of the medical image data in a phase other than that phase, and, thereafter, the final left and right ventricular regions LV, RV and the final left and right atrium regions LA, RA may be extracted using the graph cut method described above.

As described above, using the extraction results of the left and right ventricular regions LV, RV, and the left and right atrium regions LA, RA in the medical image data of one medical image in diastole, performing region extraction of medical image data in a phase other than that of the medical image data of one medical image allows region extraction of medical image data in other phases to be performed by simpler processing.

The present embodiment described above may be configured, for example, such that, if a region has not been extracted or the position of an extracted region is displaced largely as the result of the region extraction processing of the left and right ventricular regions LV, RV, and the left and right atrium regions LA, RA, a message is displayed and the region extraction processing unit 12 receives a manual correction of the positions of landmarks set when the initial region was obtained, extracts an initial region again based on the corrected positions of the landmarks, and performs the foregoing region extraction processing again. A method for receiving the manual correction of the positions of the landmarks may be, for example, displaying a correction receive screen, in which the medical image data prior to the region extraction processing are redisplayed, on the display 20 to allow the user to set-input using the input device 30.

If there is an anomaly in the extraction result of the left ventricular region, the region extraction processing unit 12 may receive a manual correction of a contour point of the left ventricular region and may extract the right ventricular region, the left atrium region, and the right atrium region using the corrected left ventricular region. The manual correction of the contour point of the left ventricular region may be performed through set-input by the user using the input device 30.

If there is an anomaly in the region extraction result in the medical image data in end-diastolic phase, the region extraction processing unit 12 may receive a manual correction of a contour point of each region in the medical image data in end-diastolic phase and may extract the right ventricular region, the left atrium region, and the right atrium region in the medical image data in a phase other than that of the medical image data of one medical image using each corrected region. The manual correction of the contour point of each region may be performed through set-input by the user using the input device 30.

Allowing a manual correction in the manner described above may reduce the time for correction.

What is claimed is:

1. A medical image processing apparatus, comprising:
   a storage device, including a medical image data obtaining unit and a region extraction processing unit; and
   a hardware processor, coupled to the storage device;
   wherein the hardware processor activates the medical image data obtaining unit for obtaining medical image data containing an image of a heart; and
   the hardware processor activates the region extraction processing unit for initially only extracting a left ventricular region that combined a contrast region and a myocardial region surrounding the contrast region of the left ventricular region of the heart among the left ventricular region, a right ventricular region, a left atrium, and a right atrium region of the heart contained in the medical image data based on the medical image data obtained by the medical image data obtaining unit by using a graph cut method, wherein processing target pixels that combined an initial region of the left ventricular region and an area surrounding the initial region are determined by using a plurality of landmarks,
   wherein after the left ventricular region of the heart had been extracted and before the right ventricular region is initially extracted, the region extraction processing unit sets an evaluation function that assigns higher costs with respect to pixels within the left ventricular region of the heart, and performs a region extraction process to extract at least one of the right ventricular region, the left atrium region, and the right atrium region of the heart by the graph cut method, wherein
   the medical image data obtaining unit obtains a plurality of medical image data in different phases of one cardiac cycle of the heart which is beating,
   the region extraction processing unit extracts a left ventricular region in medical image data of one medical image in diastole of the plurality of medical image data, then extracts, based on the extraction result of the left ventricular region, at least one of a right ventricular region, a left atrium region, and a right atrium region in the medical image data of one medical image in diastole, and extracts, based on the extraction result of the medical image data of one medical image in diastole, at least one of a right ventricular region, a left atrium region, and a right atrium region in medical image data in a phase other than that of the medical image data of one medical image in diastole, and
   the region extraction processing unit extracts a left ventricular region in medical image data of one medical image in end-diastole of the plurality of medical image data, then extracts, based on the extraction result of the left ventricular region, at least one of the right ventricular region, the left atrium region, and the right atrium region in the medical image data of one medical image in end-diastole, and extracts, based on the extraction result of the medical image data of one medical image in end-diastole, at least one of the right ventricular region, the left atrium region, and the right atrium region in medical image data in the phase other than that of the medical image data of one medical image in end-diastole.

2. The medical image processing apparatus of claim 1, wherein the region extraction processing unit limits pixels of the medical image data for a target of the region extraction processing based on the extraction result of the left ventricular region.

3. The medical image processing apparatus of claim 1, wherein the region extraction processing unit sets an evaluation function based on the extraction result of the left ventricular region and performs the region extraction processing by finding an optimal solution of the evaluation function.

4. The medical image processing apparatus of claim 1, wherein the region extraction processing unit extracts the right ventricular region based on the extraction result of the left ventricular region, and then extracts the right atrium region or the left atrium region.

5. The medical image processing apparatus of claim 1, wherein, if there is an anomaly in the extraction result of each region in the medical image data of one medical image in diastole, the region extraction processing unit receives a manual correction of a contour point of the region having the anomaly and performs the region extraction processing again for the medical image data in a phase other than that of the medical image data of one medical image in diastole based on the corrected contour point.

6. The medical image processing apparatus of claim 1, wherein the region extraction processing unit detects the landmarks in the medical image data and extracts the left ventricular region based on a detection result of the landmarks detected.

7. The medical image processing apparatus of claim 6, wherein, if the left ventricular region or the at least one region has not been extracted based on the extraction result of the plurality of landmarks, or if there is an anomaly in the left ventricular region or the at least one region extracted, the region extraction processing unit receives a manual correction of the landmarks and performs the region extraction processing again based on the corrected landmarks.

8. The medical image processing apparatus of claim 1, wherein, if the extracted left ventricular region is abnormal, the region extraction processing unit receives a manual correction of a contour point of the left ventricular region and performs the region extraction processing again for the left ventricular region based on the corrected contour point.

9. The medical image processing apparatus of claim 1, wherein the medical image data are three-dimensional image data.

10. A medical image processing method, comprising the steps of:
   obtaining, by a hardware processor, medical image data containing an image of a heart;
   initial only extracting, by the hardware processor, a left ventricular region that combined a contrast region and a myocardial region surrounding the contrast region of the left ventricular region of the heart among the left ventricular region, a right ventricular region, a left atrium, and a right atrium region of the heart contained in the medical image data based on the obtained medical image data by using a graph cut method, wherein processing target pixels that combined an initial region of the left ventricular region and an area surrounding the initial region are determined by using a plurality of landmarks,
   wherein after the left ventricular region of the heart had been extracted and before the right ventricular region is initially extracted, setting an evaluation function that assigns higher costs with respect to pixels within the left ventricular region of the heart and performing a region extraction process to extract at least one of a right ventricular region, a left atrium region, and a right atrium region by the graph cut method;
   obtaining a plurality of medical image data in different phases of one cardiac cycle of the heart which is beating;
   extracting a left ventricular region in medical image data of one medical image in diastole of the plurality of medical image data, then extracting, based on the extraction result of the left ventricular region, at least one of a right ventricular region, a left atrium region, and a right atrium region in the medical image data of one medical image in diastole, and extracting, based on the extraction result of the medical image data of one medical image in diastole, at least one of a right ventricular region, a left atrium region, and a right atrium region in medical image data in a phase other than that of the medical image data of one medical image in diastole; and
   extracting a left ventricular region in medical image data of one medical image in end-diastole of the plurality of medical image data, then extracting, based on the extraction result of the left ventricular region, at least one of the right ventricular region, the left atrium region, and the right atrium region in the medical image data of one medical image in end-diastole, and extracting, based on the extraction result of the medical image data of one medical image in end-diastole, at least one of the right ventricular region, the left atrium region, and the right atrium region in medical image data in the phase other than that of the medical image data of one medical image in end-diastole.

11. A non-transitory computer-readable recording medium containing a medical image processing program for causing a computer to function as:
   a medical image data obtaining unit for obtaining medical image data containing an image of a heart; and
   a region extraction processing unit for initially only extracting a left ventricular region that combined a contrast region and a myocardial region surrounding the contrast region of the left ventricular region of the heart among the left ventricular region, a right ventricular region, a left atrium, and a right atrium region of the heart contained in the medical image data based on the medical image data obtained by the medical image data obtaining unit by using a graph cut method, wherein processing target pixels that combined an initial region of the left ventricular region and an area surrounding the initial region are determined by using a plurality of landmarks,
   wherein after the left ventricular region of the heart had been extracted and before the right ventricular region is initially extracted, the region extraction processing unit sets an evaluation function that assigns higher costs with respect to pixels within the left ventricular region of the heart and performs a region extraction process for extracting at least one of a right ventricular region, a left atrium region, and a right atrium region of the heart by the graph cut method, wherein
   the medical image data obtaining unit obtains a plurality of medical image data in different phases of one cardiac cycle of the heart which is beating;
   the region extraction processing unit extracts a left ventricular region in medical image data of one medical image in diastole of the plurality of medical image data, then extracts, based on the extraction result of the left ventricular region, at least one of a right ventricular region, a left atrium region, and a right atrium region in the medical image data of one medical image in diastole, and extracts, based on the extraction result of the medical image data of one medical image in diastole, at least one of a right ventricular region, a left atrium region, and a right atrium region in medical image data in a phase other than that of the medical image data of one medical image in diastole; and
   the region extraction processing unit extracts a left ventricular region in medical image data of one medical image in end-diastole of the plurality of medical image data, then extracts, based on the extraction result of the left ventricular region, at least one of the right ventricular region, the left atrium region, and the right atrium region in the medical image data of one medical image in end-diastole, and extracts, based on the extraction result of the medical image data of one medical image in end-diastole, at least one of the right ventricular region, the left atrium region, and the right atrium region in medical image data in the phase other than that of the medical image data of one medical image in end-diastole.

12. A medical image processing apparatus, comprising:
   a storage device, including a medical image data obtaining unit and a region extraction processing unit; and
   a hardware processor, coupled to the storage device;
   wherein the hardware processor activates the medical image data obtaining unit for obtaining medical image data containing an image of a heart; and
   the hardware processor activates the region extraction processing unit for extracting a left ventricular region that combined a contrast region and a myocardial region surrounding the contrast region of the left ventricular region of the heart among the left ventricular region, a right ventricular region, a left atrium region, and a right atrium region of the heart contained in the medical image data based on the medical image data obtained by the medical image data obtaining unit by using a graph cut method, wherein processing target pixels that combined an initial region of the left ventricular region and an area surrounding the initial region are determined by using a plurality of landmarks, wherein after the left ventricular region of the heart had been extracted and before the right ventricular region is initially extracted, pixels which have been extracted as the left ventricular region of the heart are excluded to generate a graphical model which uses the graph cut method, and the region extraction processing unit performs a region extraction process to extract at least one of the right ventricular region, the left atrium region, and the right atrium region of the heart by the graph cut method used by the graphical model, wherein the medical image data obtaining unit obtains a plurality of medical image data in different phases of one cardiac cycle of the heart which is beating, the region extraction processing unit extracts a left ventricular region in medical image data of one medical image in diastole of the plurality of medical image data, then extracts, based on the extraction result of the left ventricular region, at least one of a right ventricular region, a left atrium region, and a right atrium region in the medical image data of one medical image in diastole, and extracts, based on the extraction result of the medical image data of one medical image in diastole, at least one of a right ventricular region, a left atrium region, and a right atrium region in medical image data in a phase other than that of the medical image data of one medical image in diastole, and the region extraction processing unit extracts a left ventricular region in medical image data of one medical image in end-diastole of the plurality of medical image data, then extracts, based on the extraction result of the left ventricular region, at least one of the right ventricular region, the left atrium region, and the right atrium region in the medical image data of one medical image in end-diastole, and extracts, based on the extraction result of the medical image data of one medical image in end-diastole, at least one of the right ventricular region, the left atrium region, and the right atrium region in medical image data in the phase other than that of the medical image data of one medical image in end-diastole.

13. A medical image processing method, comprising the steps of:

obtaining medical image data containing an image of a heart;

extracting a left ventricular region that combined a contrast region and a myocardial region surrounding the contrast region of the left ventricular region of the heart among the left ventricular region, a right ventricular region, a left atrium region, and a right atrium region of the heart contained in the medical image data based on the obtained image data by using a graph cut method, wherein processing target pixels that combined an initial region of the left ventricular region and an area surrounding the initial region are determined by using a plurality of landmarks, wherein after the left ventricular region of the heart had been extracted and before the right ventricular region is initially extracted, pixels which have been extracted as the left ventricular region of the heart are excluded to generate a graphical model which uses the graph cut method, and the region extraction processing unit performs a region extraction process to extract at least one of the right ventricular region, the left atrium region, and the right atrium region of the heart by the graph cut method used by the graphical model;

obtaining a plurality of medical image data in different phases of one cardiac cycle of the heart which is beating;

extracting a left ventricular region in medical image data of one medical image in diastole of the plurality of medical image data, then extracting, based on the extraction result of the left ventricular region, at least one of a right ventricular region, a left atrium region, and a right atrium region in the medical image data of one medical image in diastole, and extracting, based on the extraction result of the medical image data of one medical image in diastole, at least one of a right ventricular region, a left atrium region, and a right atrium region in medical image data in a phase other than that of the medical image data of one medical image in diastole; and extracting a left ventricular region in medical image data of one medical image in end-diastole of the plurality of medical image data, then extracting, based on the extraction result of the left ventricular region, at least one of the right ventricular region, the left atrium region, and the right atrium region in the medical image data of one medical image in end-diastole, and extracting, based on the extraction result of the medical image data of one medical image in end-diastole, at least one of the right ventricular region, the left atrium region, and the right atrium region in medical image data in the phase other than that of the medical image data of one medical image in end-diastole.

14. A non-transitory computer-readable recording medium containing a medical image processing program for causing a computer to function as:

a medical image data obtaining unit for obtaining medical image data containing an image of a heart; and a region extraction processing unit for extracting a left ventricular region that combined a contrast region and a myocardial region surrounding the contrast region of the left ventricular region of the heart among the left ventricular region, a right ventricular region, a left atrium region, and a right atrium region of the heart contained in the medical image data based on the medical image data obtained by the medical image data obtaining unit by using a graph cut method, wherein processing target pixels that combined an initial region of the left ventricular region and an area surrounding the initial region are determined by using a plurality of landmarks, wherein after the left ventricular region of the heart had been extracted and before the right ventricular region is initially extracted, pixels which have been extracted as the left ventricular region of the heart are excluded to generate a graphical model which uses the graph cut method, and the region extraction processing unit performs a region extraction process to extract at least one of the right ventricular region, the left atrium region, and the right atrium region of the heart by the graph cut method used by the graphical model, wherein the medical image data obtaining unit obtains a plurality of medical image data in different phases of one cardiac cycle of the heart which is beating, the region extraction processing unit extracts a left ventricular region in medical image data of one medical image in diastole of the plurality of medical image data, then extracts, based on the extraction result of the left ventricular region, at least one of a right ventricular region, a left atrium region, and a right atrium region in the medical image data of one medical image in diastole, and extracts, based on the extraction result of the medical image data of one medical image in diastole, at least one of a right ventricular region, a left atrium region, and a right atrium region in medical image data in a phase other than that of the medical image data of one medical image in diastole, and the region extraction processing unit extracts a left ventricular region in medical image data of one medical image in end-diastole of the plurality of medical image data, then extracts, based on the extraction result of the left ventricular region, at least one of the right ventricular region, the left atrium region, and the right atrium region in the medical image data of one medical image in end-diastole, and extracts, based on the extraction result of the medical image data of one medical image in end-diastole, at least one of the right ventricular region, the left atrium region, and the right atrium region in medical image data in the phase other than that of the medical image data of one medical image in end-diastole.

15. The medical image processing apparatus of claim 1, wherein the region extraction processing unit sets the plurality of landmarks, and automatically extracts positions of the landmarks by using a pattern matching; based on position information of the landmarks, the region extraction processing unit sets an initial region of the left ventricular region; the region extraction processing unit uses the graph cut method of extract a final left ventricular region by using pixels in the initial region and pixels in an area surrounding the initial region.

16. The medical image processing apparatus of claim 12, wherein the region extraction processing unit sets the plurality of landmarks, and automatically extracts positions of the landmarks by using a pattern matching; based on position information of the landmarks, the region extraction processing unit sets an initial region of the left ventricular region; the region extraction processing unit uses the graph cut method of extract a final left ventricular region by using pixels in the initial region and pixels in an area surrounding the initial region.

17. The medical image processing apparatus of claim 1, wherein a graphical model utilized by the graph cut method is generated by linking each of the processing target pixels with a first link or a second link, wherein the first link represents that the processing target pixel is associated to the left ventricular region, and the second link represents that the processing target pixel is associated a region other than the left ventricular region.

18. The medical image processing apparatus of claim 12, wherein the graphical model is generated by linking each of the processing target pixels with a first link or a second link, wherein the first link represents that the processing target pixel is associated to the left ventricular region, and the second link represents that the processing target pixel is associated a region other than the left ventricular region.

* * * * *